(12) United States Patent
Ozeki et al.

(10) Patent No.: US 8,293,269 B2
(45) Date of Patent: *Oct. 23, 2012

(54) COMPOSITIONS FOR PROMOTING SLEEP

(75) Inventors: Makoto Ozeki, Yokkaichi (JP); Haruo Yao, Yokkaichi (JP); Tsutomu Okubo, Yokkaichi (JP); Lekh Raj Juneja, Yokkaichi (JP)

(73) Assignee: Taiyo Kagaku Co., Ltd., Yokkaichi-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/843,913

(22) Filed: Aug. 23, 2007

(65) Prior Publication Data

US 2008/0039526 A1    Feb. 14, 2008

Related U.S. Application Data

(63) Continuation of application No. 09/980,620, filed as application No. PCT/JP01/02916 on Apr. 4, 2001, now Pat. No. 7,273,621.

(30) Foreign Application Priority Data

Apr. 5, 2000 (JP) ................................. 2000-102926

(51) Int. Cl.
*A61K 9/48* (2006.01)
*A61K 9/00* (2006.01)
*A01N 65/00* (2009.01)

(52) U.S. Cl. .......................... 424/451; 424/400; 424/725

(58) Field of Classification Search ....................... None
See application file for complete search history.

(56) References Cited

U.S. PATENT DOCUMENTS

| 5,501,866 | A | 3/1996 | Kakuda et al. |
| H1628 | H | 1/1997 | Ekanayake et al. |
| 5,736,575 | A | 4/1998 | Kakuda et al. |
| 6,271,259 | B1 * | 8/2001 | Kakuda et al. ............... 514/563 |
| 6,589,566 | B2 | 7/2003 | Ueda et al. |
| 6,831,103 | B1 * | 12/2004 | Ueda et al. |
| 7,273,621 | B2 * | 9/2007 | Ozeki et al. |
| 2001/0001307 | A1 | 5/2001 | Ueda et al. |
| 2002/0122835 | A1 | 9/2002 | Bucci et al. |
| 2005/0191341 | A1 * | 9/2005 | Kellermann ................. 424/450 |
| 2005/0282865 | A1 * | 12/2005 | Furukawa et al. ............ 514/343 |

FOREIGN PATENT DOCUMENTS

| EP | 1057483 A1 | 12/2000 |
| JP | 05-068578 A | 3/1993 |
| JP | 05-123166 A | 5/1993 |
| JP | 07-022749 A | 4/1995 |
| JP | 09-012454 A | 1/1997 |
| WO | WO-99/42096 A1 | 8/1999 |

OTHER PUBLICATIONS

Python et al., "Extracellular serotonin variations during vigilance states in the preoptic area of rats: a microdialysis study", 2001, Brain Research, 910: 49-54.*
Uchida et al., "Flunitrazepam Effects on Human Sleep EEG Spectra: Differences in NREM, REM and Individual Responses", 1996, Life Sciences, 58(10): PL 199-205.*
Wauquier, A. and C. Dugovic, "Serotonin and Sleep-Wakefulness", 1990, Annals of the New York Academy of Sciences, 600: 447-458.*
Yokogoshi et al., "Effect of Theanine, r-Glutamylethylamide, on Brain Monoamines and Striatal Dopamine Release in Conscious Rats", 1998, Neurochemical Research, 23(5): 667-673.*
Sagesaka et al., "Pharmacological Effect of Theanine", Ito-en Central Research Institute, pp. 362-365.*
Kimura et al., Chem. Pharm. Bull., vol. 19, No. 7, pp. 1301-1307 (1971).
Japanese Application No. 2001-572097; Office Action; May 12, 2011; pp. 1-3.

* cited by examiner

*Primary Examiner* — Robert A Wax
*Assistant Examiner* — Randeep Singh
(74) *Attorney, Agent, or Firm* — Birch, Stewart, Kolasch & Birch, LLP

(57) ABSTRACT

An object of the present invention is to provide a composition for promoting sleep, which any one can safely take on a daily basis without any risks of adverse action. In addition, an object of the present invention is to provide food and a medicament, comprising the above-mentioned composition, having an effect for promoting sleep for an individual having sleep disorders. Further, an object of the present invention is to provide a method for promoting sleep comprising administering theanine to an individual having sleep disorders, and use of theanine for preparation of the food or medicament for an individual having sleep disorders.

4 Claims, No Drawings

US 8,293,269 B2

COMPOSITIONS FOR PROMOTING SLEEP

CROSS-REFERENCE TO RELATED APPLICATIONS

The present application is a Continuation of co-pending U.S. application Ser. No. 09/980,620, filed on Dec. 5, 2001 now U.S. Pat. No. 7,273,621, which is a national phase under 35 U.S.C. §371 of PCT International Application No, PCT/JP01/02916 which has an International filing date of Apr. 4, 2001, which claims priority of Application No, 2000-102926 filed in Japan on Apr. 5, 2000 under 35 U.S.C. §119, the entire contents of which are hereby incorporated by reference and for which priority is claimed under 35 U.S.C. §120.

TECHNICAL FIELD

The present invention relates to a composition for promoting sleep, comprising theanine, food and a medicament each comprising the composition, a method for promoting sleep using theanine, and use of theanine for preparation of the above-mentioned food or medicament.

BACKGROUND ART

Sleep disorders are disorders which will be an entrance for alcohol dependence of drug such as narcoleptics, narcotism, and the like. Therefore, the way of overcoming the sleep disorders would associate with prevention of these problems, thereby making it socially significant. At present, a therapeutic medicament such as Halcion or Listomin S has been used against the sleep disorders described above. However, there are some defects such that these medicaments have undesirable adverse action such as dizziness, amnesia and emotional instability due to the dependence, so that it would be extremely risky to take these medicaments without any instructions from a physician, and not all those individuals having sleep disorders can take the medicaments. As described above, there are some defects such that conventional synthetic medicaments have adverse action. Thus, an effective method of treatment has not yet been found so far.

DISCLOSURE OF INVENTION

An object of the present invention is to provide a composition for promoting sleep, which any one can safely take on a daily basis without any risks of adverse action. In addition, an object of the present invention is to provide food and a medicament, having an effect for promoting sleep for an individual having sleep disorders. Further, an object of the present invention is to provide a method for promoting sleep effective for an individual having sleep disorders, and use of theanine for preparation of the above-mentioned food or medicament.

The present inventors have intensively studied in order to solve the above-mentioned problems. As a result, they have found that theanine is effective for promoting sleep without accompanying adverse action which had been problematic. The present invention has been perfected thereby.

Specifically, the present invention relates to:
[1] a composition for promoting sleep, comprising theanine;
[2] food comprising the composition of item [1] above for an individual having sleep disorders;
[3] a medicament comprising the composition of item [1] above for an individual having sleep disorders;
[4] a method for promoting sleep in an individual having sleep disorders, comprising administering theanine to the individual having sleep disorders; and
[5] use of theanine for preparation of food or a medicament for an individual having sleep disorders.

BEST MODE FOR CARRYING OUT THE INVENTION

The composition for promoting sleep of the present invention (hereinafter referred to as "composition") can be used on a daily basis for the purpose of moderating or ameliorating various sleep disorders generated by various causations. The desired effects of the composition of the present invention are exhibited on the basis of the action for promoting sleep found for the first time in theanine, which is contained in the composition.

Theanine used in the present invention is a glutamic acid derivative (γ-glutamylethylamide), which is an amino acid component naturally contained largely in tea-leaves. Although there have not yet been elucidated many parts in the action mechanism for the sleep promoting action by theanine found in the present invention, it has been known that it is assumed that the above-mentioned action is exhibited through some sort of influences of the theanine to the changes in the brainwaves, which have been known to take place in such a manner that a ratio occupied by α-waves decrease in Stage 1 and δ waves increase, in 6 sleep stages comprising Stage W, Stage 1, Stage 2, Stage 3, Stage 4 and Stage REM. In other words, the term "promoting sleep" in the present specification refers to promoting a natural progression of sleep with maintaining homeostasis of a living body regarding sleep. Therefore, the composition of the present invention can be used on a daily basis as desired without any concerns on the occurrence of adverse action such as dependence. For instance, the composition of the present invention comprising theanine can be used, for instance, to moderate or ameliorate various sleep disorders caused by changes in the body rhythm, such as insomnia, sleeplessness (difficulty in failing asleep), vigilance in middle of sleep, vigilance in early morning, and disturbance of restful sleep.

The exhibition of the sleep promoting action of the theanine used in the present invention is determined by evaluating changes in the brainwaves in the sleep introductory stage by polygraph. In other words, when the changes in the brainwaves are found in the above-mentioned sleep introductory stage, it is evaluated to have entered sleeping state. The time periods until entering the sleeping state are compared between an individual administered with the theanine and an individual without administration. When the individual administered with the theanine enters the sleeping state earlier than the individual without administration, it is judged that the sleep promoting action of the theanine is exhibited. In addition, according to the polygraph, since phenomena of a living body such as electrocardioagram, oculograph, electromyogram, and pneumogram as well as the brainwaves can be also simultaneously recorded and observed, the exhibition of the sleep promoting action of the theanine can be also judged by those items other than the brainwaves.

Methods for preparing theanine used in the present invention may be any of known methods, including a method of extracting from tea-leaves; an organic synthesis method [*Chem. Pharm. Bull.*, 19(7), 1301-1307 (1971)]; methods of treating a mixture of glutamine and ethylamine with glutaminase (Japanese Examined Patent Publication No, Hei 7-55154); a method comprising culturing cultured cells of tea in a medium containing ethylamine, thereby achieving growth promotion of the cultured cells while increasing the cumulative amount of theanine in the cultured cells (a plant cell culture method) (Japanese Patent Laid-Open No. Hei 5-123166); modification methods in which ethylamine is substituted by an ethylamine derivative such as ethylamine hydrochloride in the above-mentioned plant cell culture method disclosed in Japanese Examined Patent Publication No. Hei 7-55154 or Japanese Patent Laid-Open No Hei 5-123166; and the like. In addition, the theanine used in the present invention may be of any forms, such as purified products, crudely purified products, extracts, and the likes. The "tea-leaves" as referred to herein include green tea-leaves, oolong tea-leaves, black tea-leaves, and the like. Also, a commercially available product [SUNTHEANINE (registered trade mark), manufactured by Taiyo Kagaku Co., Ltd.] may be used.

In addition, any of L-theanine, D-theanine and DL-theanine can be used, among which the L-form is preferred in the present invention, because it is approved as a food additive, and is economically utilizable.

The content of the theanine in the composition of the present invention is not particularly limited, and it may be appropriately adjusted as desired. For example, the preferred content of the theanine in the composition is from 5 to 100% by weight, more preferably from 50 to 100% by weight.

The composition of the present invention may further comprise any kinds of various minerals. The composition comprising a mineral is more preferable, because there is exhibited such an effect that the composition can supply a living body with essential elements and trace essential elements, which tend to be deficient in living bodies. The mineral content in the composition, for example, is preferably from 0-0001 to 99.9% by weight and more preferably from 0.01 to 99.9% by weight. The mineral includes metals or metal salts essential for maintaining and regulating homeostasis of living bodies, such as iron, magnesium, copper, zinc, selenium, calcium, potassium, manganese, chromium, iodine, molybdenum, nickel and vanadium, or salts thereof. These minerals may be used alone or in admixture of two or more metal elements.

Crude medicines, herbs, amino acids, vitamins, etc. may also be contained. Such crude medicines preferably include, but are not limited to, reisi (*ganoderma*), rehmannia root, and common jujube, which are effective in stabilizing mental conditions. Herbs include, but are not limited to, anise, carrot seed, clove, coriander, cypress, cinnamon, juniper, ginger, sweet orange, pine needle, basil, patchouli, bitter orange, fennel, black pepper, bay, peppermint, bergamot, mandarin, myrrh, lemongrass, rosemary, grapefruit, cedarwood, citronella, sage, thyme, tea tree, violet leaf, vanilla, hyssop, eucalyptus, lime, lemon, ylang-ylang, cardamon, clary sage, jasmine, geranium, chamomile, Bulgarian rose, rose, olibanum, lavender, chamomile, geranium, sandalwood neroli, verbena, petigrain, vetiver, majoram, lemon balm (*Melissa officinalis*), rosewood, *Hypericum*, St, John's wort, and kawakawa, with preference given to peppermint, bergamot, ylang-ylang, geranium, chamomile, lavender, St. John's wort, and kawakawa, which have sedative and relaxation effects. The forms of these herbs include, but are not limited to, extract, essential oil, and herb tea. Amino acids include, but are also not limited to, for example, glutamine, glutamic acid, tryptophan, alanine, arginine, aspartic acid, threonine, serine, γ-aminobutyric acid, taurine, thiotaurine, and hypotaurine. Vitamins include, but are not limited to, for example, vitamin A, vitamin $B_1$, vitamin $B_2$, vitamin $B_6$, vitamin $B_{12}$, vitamin C, vitamin D, vitamin E, vitamin K, folic acid, nicotinic acid, lipoic acid, pantothenic acid, biotin, ubiquinone, and prostaglandin, as well as derivatives of these vitamins. In addition to these ingredients, there may be used preferably, for example, aloe, royal jelly, melatonin, placenta, propolis, isoflavone, soybean lecithin, egg yolk lecithin, egg yolk oil, chondroitin, cacao mass, collagen, vinegar, chlorella, spirulina, gingko leaf, green tea, tochu tea (*Eucommia ulmoides*), Chinese wolfberry tea, oolong tea, mulberry leaf, Rubus suavissimus (tencha), banaba tea, unsaturated fatty acids, saccharides such as oligosaccharides, microorganisms such as bifidobacteria and red koji; mushrooms such as agaricus (*Agaricus blazei*), and Grifola frondosa; fruits such as blueberry, prune, grape, olive, Japanese apricot, and citruses; seeds such as peanut, almond, sesame, and pepper; vegetables such as green pepper, chili, Welsh onion, pumpkin, gourd, carrot, burdock, jute leaf (*Corchorus capsularis*), garlic, perilla, wasabi, tomato, scallion, leaf vegetables, tubers, and beans; seaweeds such as wakame; fishes; meat, poultry, and whale meat; and cereals; as well as their extracts, dried products, crudely purified products, purified products, processed products, and fermented products and other products therefrom.

In addition, in one embodiment of the present invention, there is provided food or a medicament comprising the composition of the present invention for an individual having sleep disorders, which is suitable for daily use. The food or medicament mentioned above is not particularly limited as long as it comprises a composition comprising theanine. Here, the term "individual" in the present specification includes, for instance, mammal, concretely human, pigs, bulls and cows, dogs, cats, horses, and the like, and especially human is preferable.

The food of the present invention includes various foods comprising theanine which are exemplified below.

The foods include, for instance, solid foods and liquid foods such as soft drinks, mineral water, luxury beverages, and alcoholic beverages. The liquid foods to be listed herein are not particularly limited, and include teas, such as green tea, oolong tea, black tea and herb tea, fruit juice concentrates, reconstituted juice concentrates, fresh juices, mixed fruit juices, fruit grain-containing fruit juice, fruit juice-containing beverages, mixed fruit/vegetable juice, vegetable juice, mineral water, carbonated beverages, soft drinks, milk, milk beverages, Japanese sake, beer, wine, cocktails, shochu, whiskey and the like. In addition, the solid foods are not particularly limited, and preferred ones are paste products soybean processed products, moose, jelly, yogurt, cold confectionaries, candies, chocolates, chewing gums, crackers, biscuits, cookies, cakes, bread, and the like.

In addition, the medicament of the present invention is not particularly limited, as long as the medicament comprises theanine. For instance, the medicament may be of any forms such as solutions, suspensions, powders, and solid molded products. The preparation forms of the medicament include, for instance, tablets, capsules, powders, granules, beverages, and the like. Also, the medicament can be used together with other medicaments.

The above-mentioned food or medicament of the present invention encompasses those which are used for individuals other than human. For instance, there can be included feeds, beverages, preparations, reagents and the like having sleep promoting effects favorably used for mammalian animals having sleep disorders, such as livestock such as bulls and cows, pigs, and horses, and pets such as dogs and cats.

The method for preparing the composition of the present invention is not particularly limited. For instance, general methods for preparing food or a medicament may be used, including a method comprising powder-mixing theanine with other raw materials; a method comprising dissolving theanine and other raw materials in a solvent to give a mixed solution; a method comprising lyophilizing the resulting mixed solution; a method comprising spray-drying the resulting mixed solution; and the like. The same methods can be applied for the food or medicament of the present invention. In addition, the components other than theanine which can be used when the composition of the present invention is prepared can be selected appropriately in accordance with the desired use, so long as the exhibition of the desired effects by the theanine is not inhibited.

For instance, the food of the present invention can be prepared by adding theanine to the conventional food by a conventional method so that the content of the theanine in the food of the present invention after the preparation is preferably within the above-mentioned range of the preferred content of the theanine in the composition. In addition, the medicament of the present invention can be prepared by formulating theanine by a conventional method, together with, for instance, a known organic or inorganic vehicle, excipient, binder, stabilizing agent, suitable for oral administration, and the like, so that the content of the theanine in the medicament of the present invention is preferably within the above-mentioned range of the preferred content of the theanine in the composition as in the case of preparation of the food. Use of the theanine in the preparation of the food or medicament of the present invention for an individual having sleep disorders is also encompassed in the present invention.

Further, in one embodiment of the present invention, there is provided a method for promoting sleep in an individual having sleep disorders, comprising administering theanine to the individual having sleep disorders. According to the method, since the sleep of an individual can be promoted safely and effectively, without any concerns on the generation of adverse action, the method is effective for moderating or ameliorating sleep disorders of the individual. In this embodiment, in general, the effective dosage of the theanine for obtaining the desired effects of the present invention is, for instance, preferably from 0.2 to 200 mg/kg weight, more preferably from 0.5 to 50 mg/kg weight for an adult per day in a case of human. However, since each individual has different kind and extent of sleep disorder and individual differences (age, sex and the like), the dosage of the theanine in the present invention is not limited to those ranges given above.

As to the administration of the theanine, theanine per se may be administered, or the composition of the present invention, preferably the food or medicament, may be administered. Also, the administration methods, the number of administration, the administration period, and the like are also not particularly limited. For instance, the theanine is administered within the above-mentioned effective dosage range at once or divided in plural times, preferably by oral administration, to the above-mentioned individual, preferably human desiring to moderate or ameliorate sleep disorders. The theanine or the composition of the present invention or the like can be, for instance, taken on a daily basis, whereby preventing sleep disorders.

The safety of the theanine used in the present invention is high. For instance, in an acute toxic test using mice, there are no death cases when mice are administered orally at 5 g/kg, so that there are found no abnormality in the general state and body weight. In addition, especially L-theanine is known as the main component of deliciousness (umami) of tea, and is also used as a food additive for the use of deliciousness, and there is no limitation in its amount according to the Japanese Food Sanitation Act. Moreover, contrary to the conventional medicament for ameliorating sleep disorders, since dependence on the theanine is not found at all, the sleep can be promoted safely and effectively by the use of the composition, food or medicament of the present invention, whereby moderating or ameliorating the sleep disorders.

EXAMPLES

Next, the present invention will be described in further detail by means of Examples, without intending to limit the scope of the present invention to these Examples alone. In Examples, the expression "parts" means "parts by weight" unless specified otherwise.

Production Example 1

0.3 M glutamine and 1.5 M ethylamine were allowed to react at 30° C. for 22 hours in borate buffer ($Na_2B_4O_7$—NaOH, pH=11) in the presence of 0.3 U glutaminase [manufactured by Amano Seiyaku K.K.]. Subsequently, the reaction mixture was subjected to column chromatography using Dowex 50×8 and Dowex 1×2 [both being manufactured by Muromachi Kagaku Kogyo K.K.]. The resulting product was treated with ethanol to isolate the desired substance from the reaction mixture.

The obtained substance was confirmed as L-theanine by subjecting the resulting isolated substance to amino acid analyzer and paper chromatography, whereby confirming that the obtained substance exhibits the same behaviors as the standard substance. When the obtained substance was subjected to hydrolysis treatment with hydrochloric acid or glutaminase, glutamic acid and ethylamine were generated at a ratio of 1:1 (molar ratio). As described above, since the isolated substance was hydrolyzed by glutaminase, it is shown that ethylamine was bonded at the γ-position of glutamic acid. In addition, it was also confirmed by using the glutamic acid dehydrogenase that glutamic acid generated by hydrolysis had an L-form. From the above, the resulting isolated substance was confirmed to be L-theanine.

From the above steps, 225 nmol of L-theanine was obtained A by-product glutamic acid was 20 nmol.

Production Example 2

Ten kilograms of tea leaves (*Camellia sinensis* L.) were subjected to extraction with boiling water. The resulting extract was applied to a cationic exchange resin ("Dowex HCR W-2," manufactured by Muromachi Kagaku Kogyo K.K.), and eluted with 1 N NaOH. The eluted fraction was applied to an activated carbon ("Taiko Kasseitan SG" manufactured by Futamura Kagaku Kogyo K.K.), and eluted with 15% ethanol. The resulting eluted fraction was concentrated with an RO membrane (manufactured by NITTO DENKO CORPORATION "NTR 729 HF"), and then purified by column chromatography. Furthermore, the purified product was recrystallized, to give 24-8 g of L-theanine.

Example 1

Theanine-containing candies were produced in accordance with the composition shown below by using the L-theanine prepared in Production Example 1.

| Theanine-Containing Candies | |
|---|---|
| 1. Granulated Sugar | 64 parts |
| 2. Malt Syrup | 23 parts |

-continued

| Theanine-Containing Candies | |
|---|---|
| 3. L-Theanine | 10 parts |
| 4. Flavor (Lemon Flavor) | 0.05 parts |
| 5. Tartaric acid | 1 part |
| 6. Water | 30 parts |

The granulated sugar was completely dissolved in 20 parts of water with heating to 110° C. The malt syrup was added thereto, and the temperature was raised to 145° C. After heating was stopped, the tartaric acid was added thereto and mixed, and the remaining water after L-theanine was previously dissolved was added thereto. The mixture was mixed again, cooled to 75° to 80° C., and formed with a molding roller, to prepare theanine-containing candies each drop weighing 1 g.

Example 2

Theanine-containing capsules were produced in accordance with the composition shown below by using the L-theanine prepared in Production Example 2.

| Theanine-Containing Capsules | |
|---|---|
| 1. L-Theanine (manufactured by Taiyo Kagaku Co., Ltd.) | 98 parts |
| 2. Gum Arabic (manufactured by Gokyo Sangyo K.K.) | 2 parts |

The L-theanine powder was coated with the gum arabic by a conventional method, to give theanine-containing capsules.

Example 3

One drop of candy produced in Example 1 was given to each of 5 panelists who had been suffering from sleeplessness, i.e. those individuals who could not fall asleep within the time range of 1 hour or more and less than 1.5 hours after getting set to bed, the candy being given 30 minutes before getting set to bed. The sleeplessness of 2 panelists was ameliorated on 4 day of candy intake, and all members of the panelists were ameliorated in the sleeplessness on 12 day, i.e. those individuals could fall asleep within 20 minutes or so after getting set to bed. In addition, undesired adverse action was not observed at all.

A half month before carrying out the test, a similar test was carried out with a capsule (placebo) in which theanine in the theanine-containing capsule was substituted with lactose. However, none of the individuals showed any ameliorations in the sleeplessness.

Example 4

One theanine-containing capsule obtained in Example 2 (L-theanine: 200 mg/one capsule) was given to each of 3 panelists who had been diagnosed as insomnia, ice those individuals who could not fall asleep over a time period of 1.5 hours or more after getting set to bed, the capsule being given 30 minutes before after getting set to bed. The insomnia was eliminated on 4 day of capsule intake in 2 panelists, and the insomnia was eliminated on 12 day in all 3 panelists, i.e. those individuals could fall asleep within 20 minutes or so after getting set to bed. In addition, undesired adverse action was not observed at all.

A half month prior to carrying out the test, a similar test was carried out with a capsule (placebo) in which theanine in the theanine-containing capsule was substituted with lactose. However, none of the individuals showed any ameliorations in the insomnia.

INDUSTRIAL APPLICABILITY

According to the present invention, there is provided a composition for promoting sleep, which any one can safely take on a daily basis without any risks of adverse action. In addition, according to the present invention, there is provided food and a medicament, having an effect for promoting sleep for an individual having sleep disorders. Further, according to the present invention, there is provided a method for promoting sleep comprising administering the theanine to an individual having sleep disorders.

The invention claimed is:

1. A method for moderating or ameliorating vigilance in middle of sleep, comprising administering to a human suffering from vigilance in middle of sleep a preparation comprising an amount of 0.2 to 50 mg theanine/kg per day, wherein said preparation is in a form selected from the group consisting of tablets, capsules, powders, granules and beverages.

2. The method according to claim 1, wherein the preparation is administered 30 minutes before getting set to bed.

3. A method for treating a human who cannot fall asleep within the time range of 1 hour or more and less than 1.5 hours after getting set to bed, comprising administering to the human a preparation comprising an amount of 0.2 to 50 mg theanine/kg per day, whereby the human falls asleep within about 20 minutes after getting set to bed.

4. The method according to claim 3, wherein the preparation is administered 30 minutes before getting set to bed.

* * * * *